(12) United States Patent
Corcoran et al.

(10) Patent No.: US 7,566,336 B2
(45) Date of Patent: Jul. 28, 2009

(54) LEFT ATRIAL APPENDAGE CLOSURE DEVICE

(75) Inventors: Michael P. Corcoran, Woodbury, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 700 days.

(21) Appl. No.: 10/721,723

(22) Filed: Nov. 25, 2003

(65) Prior Publication Data

US 2005/0113861 A1    May 26, 2005

(51) Int. Cl.
    *A61B 17/08* (2006.01)
(52) U.S. Cl. ..................................... 606/151
(58) Field of Classification Search ............ 606/151, 606/157, 158, 113, 127, 213, 214, 153
    See application file for complete search history.

(56) References Cited

U.S. PATENT DOCUMENTS

| 3,874,388 A | 4/1975 | King et al. |
| 4,007,743 A | 2/1977 | Blake |
| 4,917,089 A | 4/1990 | Sideris |
| 5,108,420 A | 4/1992 | Marks |
| 5,171,259 A | 12/1992 | Inoue |
| 5,284,488 A | 2/1994 | Sideris |
| 5,334,137 A | 8/1994 | Freeman |
| 5,334,217 A | 8/1994 | Das |
| 5,397,331 A | 3/1995 | Himpens et al. |
| 5,425,744 A | 6/1995 | Fagan et al. |
| 5,433,727 A | 7/1995 | Sideris |
| 5,451,235 A | 9/1995 | Lock et al. |
| 5,634,936 A | 6/1997 | Linden et al. |
| 5,702,421 A | 12/1997 | Schneidt |
| 5,709,707 A | 1/1998 | Lock et al. |
| 5,725,552 A | 3/1998 | Kotula et al. |
| 5,741,297 A | 4/1998 | Simon |
| 5,846,260 A * | 12/1998 | Maahs ..................... 606/200 |
| 5,904,703 A | 5/1999 | Gilson |
| 6,024,756 A | 2/2000 | Huebsch et al. |
| 6,174,322 B1 | 1/2001 | Schneidt |
| 6,206,907 B1 | 3/2001 | Marino et al. |
| 6,379,368 B1 | 4/2002 | Corcoran et al. |
| 6,635,066 B2 * | 10/2003 | Tanner et al. ............ 606/151 |
| 6,652,555 B1 | 11/2003 | VanTussel et al. |
| 6,656,206 B2 * | 12/2003 | Corcoran et al. ......... 606/151 |

FOREIGN PATENT DOCUMENTS

| DE | 233 303 | 2/1986 |
| DE | 42 22 291 C1 | 1/1994 |
| EP | 0 362 113 | 4/1993 |
| EP | 0 541 063 | 9/1998 |
| GB | 2 269 321 A | 9/1994 |

* cited by examiner

*Primary Examiner*—Kevin T Truong
(74) *Attorney, Agent, or Firm*—Kinney & Lange, P.A.

(57) ABSTRACT

This invention relates to an occlusion device for the closure of a physical lumen. More specifically, this invention relates to an occlusion device for the left atrial appendage of the heart, comprising a center post, a plurality of ribs extending along the center post and sheet which is attached to the ribs.

47 Claims, 6 Drawing Sheets

LEFT ATRIAL APPENDAGE CLOSURE DEVICE

CROSS-REFERENCE TO RELATED APPLICATION(S)

None.

BACKGROUND OF THE INVENTION

This invention relates to an occlusion device for the closure of a physical lumen. More specifically, this invention relates to an occlusion device for the left atrial appendage of the heart.

The heart is generally comprised of four chambers: the left and right atrium, and the left and right ventricle. Additionally, a small cavity called the left atrial appendage (LAA) is located off the left atrium between the mitral valve and the left pulmonary vein. Thus, the LAA opens into the left atrium of the heart. The LAA is shaped like a small thumb which terminates as it tapers away from the opening.

In a healthy heart, the LAA contracts as the heart contracts. In individuals diagnosed with atrial fibrillation (AF), however, the LAA may not contract with enough force to expel all of the blood from the LAA. In individuals diagnosed with AF, the electrical activity of the atrium becomes very rapid and disorganized. Thus, the heart beats quickly and may not get enough time in between beats to fill up with blood. As a result, only a small amount of blood is pumped out of the heart with each beat, and the cardiac output drops significantly. Therefore, stagnant blood may easily remain in the LAA. Because clotting occurs when blood is stagnant, clots or thrombi may form in the LAA. If a blood clot leaves the LAA and becomes lodged in an artery in the brain, a stroke results.

Approximately 15 percent of strokes occur in people diagnosed with AF. Approximately 2 million Americans have been diagnosed with AF. Studies indicate that more than 90 percent of non-rheumatic atrial fibrillation related strokes result from a blood clot that has formed in the left atrial appendage. Anti-clotting drugs may be used to prevent strokes in patients diagnosed with AF. However, many people cannot take such drugs because of potential side effects. Drug therapy may also cause bleeding and may be difficult to control because determining dosage is challenging. Recent studies indicate that elimination of the LAA, through occlusion or closure, may prevent thrombi from forming in the LAA and thus may reduce the incidence of stroke in patients diagnosed with AF. As such, occlusion or closure of the LAA may significantly reduce the incidence of stroke in patients with atrial fibrillation and without the complications of drug therapy.

The LAA may be sealed off during open heart surgery, which is a risky, painful, and expensive procedure. Surgery for closure of the LAA is major heart surgery, which requires the patient to undergo general anesthesia and opening of the chest cavity. The patient must spend several days in the hospital and thereafter may take several weeks to be able to return to normal levels of activity.

To avoid the risks and discomfort associated with open heart surgery, modern occlusion devices have been developed that are small, implantable devices capable of being delivered to the heart through a catheter. Rather than surgery, a catheter inserted into a major blood vessel allows an occlusion device to be deployed at the defect once the device has been moved through the catheter to the treatment site. This procedure is performed in a cardiac cathlab and avoids the risks and pain associated with open heart surgery. These devices have proven effective at sealing defects in the heart and could likewise be used to occlude the LAA without requiring open heart surgery.

Thus, there is a need in the art for a LAA occlusion device which can be implanted using a catheter to avoid heart surgery and which may provide an alternative to drug therapy.

BRIEF SUMMARY OF THE INVENTION

This invention relates to an occlusion device for the closure of a physical lumen. More specifically, this invention relates to an occlusion device for the left atrial appendage of the heart which comprises a center post, a plurality of ribs extending from the proximal end to the distal end of the center post, and a sheet which is attached to the ribs. Radial pressure from the ribs secures the device in the left atrial appendage and the sheet prevents blood from entering the left atrial appendage. Thus, thrombi formation in the left atrial appendage may be reduced.

DETAILED DESCRIPTION

Figure 1:
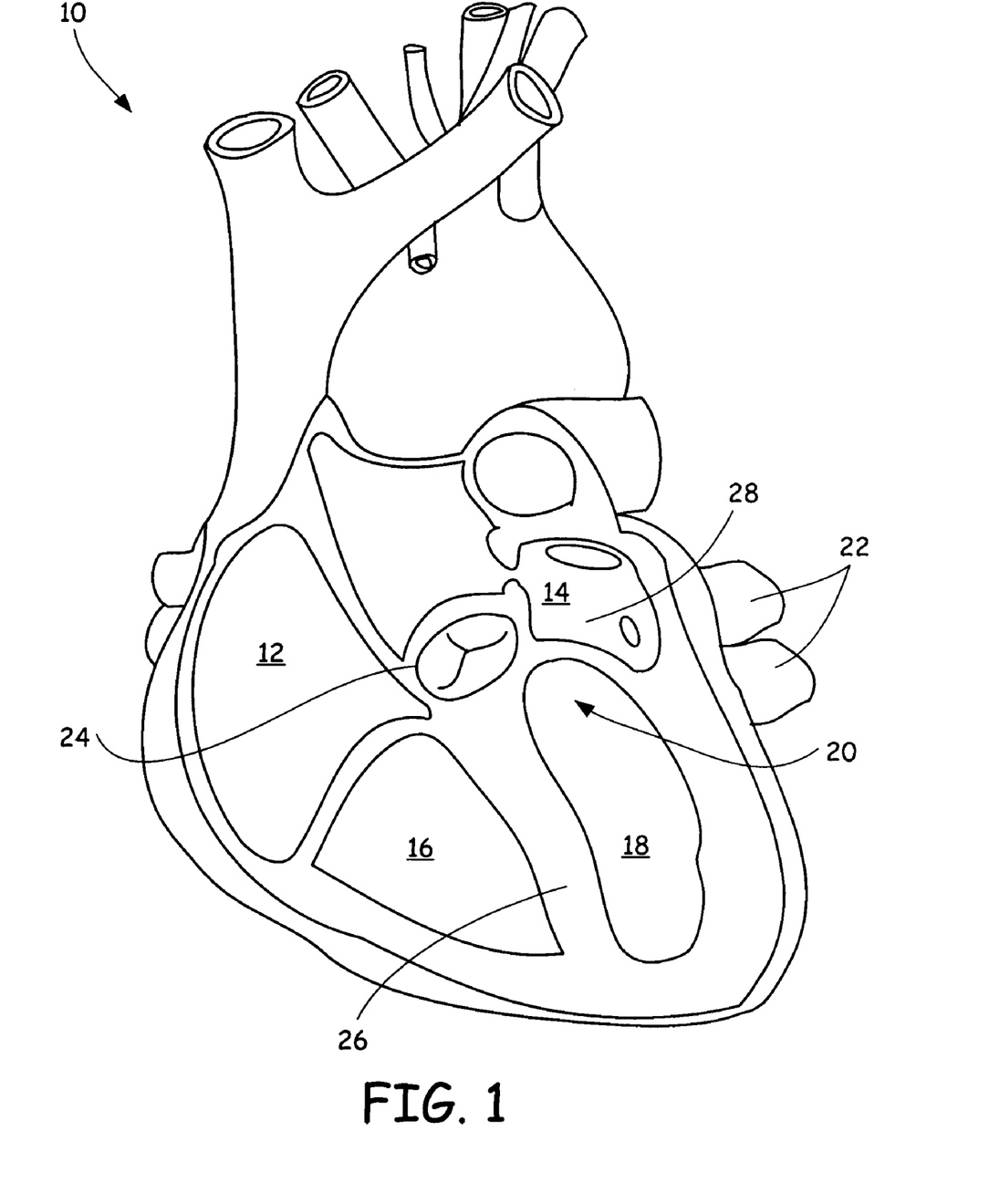
FIG. 1 is a diagram of a human heart.

FIG. 1 is a diagrammatic view of a human heart 10. Visible in FIG. 1 is right atrium 12, left atrium 14, right ventricle 16, left ventricle 18, mitral valve 20, and left pulmonary veins 22. The right atrium 12 is separated from the left atrium 14 by an atrial septal wall 24. The right ventricle 16 is separated from the left ventricle 18 by a ventricular septal wall 26. The approximate location 28 of the left atrial appendage (LAA) 28 is also shown. As mentioned previously, the LAA does not contract with force in patients diagnosed with AF and clots may form in the LAA as a result. Elimination or closure of the LAA through the use of the present invention prevents clot formation in the LAA.

The occlusion device may be deployed in the LAA through percutaneous transcatheter delivery or open heart surgery. Preferably, the device is delivered via catheter because it is a less risky, less invasive procedure. To deliver the device to the LAA via catheter, a catheter may be inserted into a patient's vasculature and advanced into the right atrium 12. A needle may then be advanced through the catheter and used to puncture the atrial septal wall 24 so that the catheter may be passed into the left atrium 14. If a defect in the atrial septal wall exists 24, such as an atrial septal defect, the catheter may be passed through the defect, eliminating the need to puncture the atrial septal wall 24. After the catheter is passed through the atrial septal wall 24, the catheter is advanced to the left atrium 14. The occlusion device may then be deployed via the catheter into the LAA.

Figure 2:
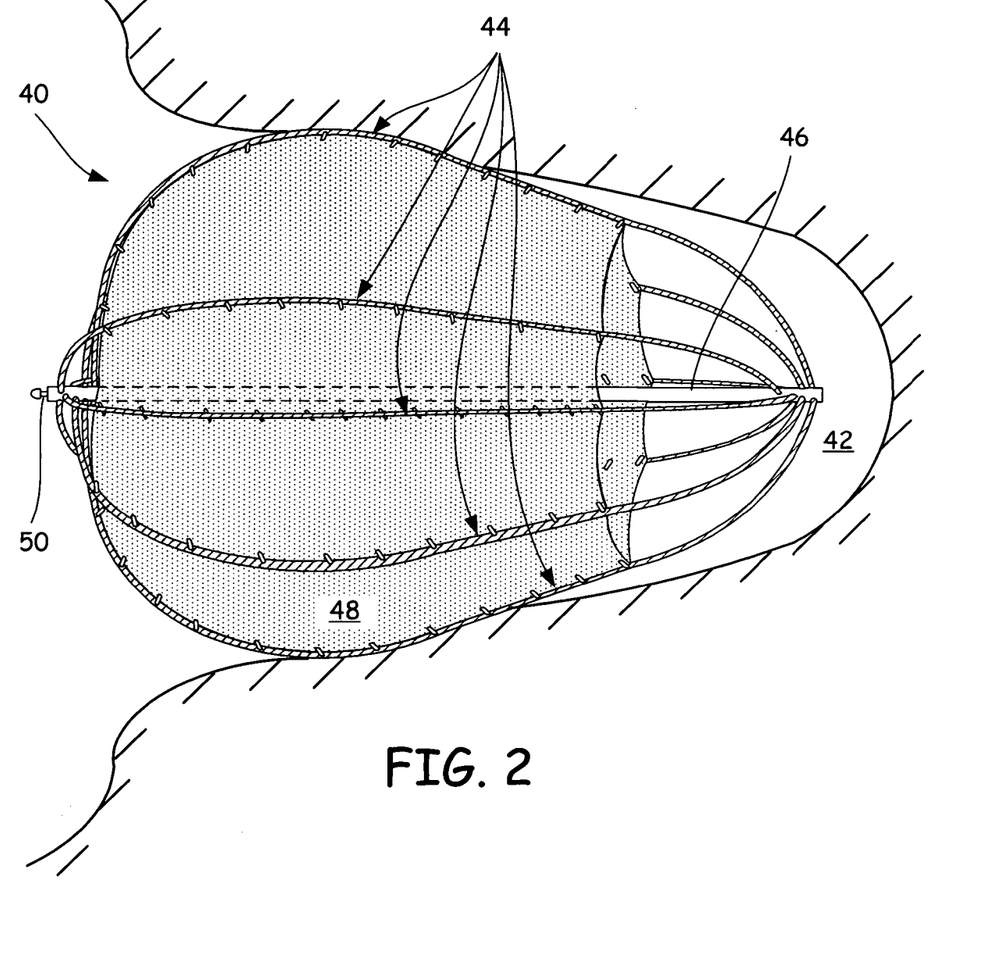
FIG. 2 is a diagram of an occlusion device in place in a left atrial appendage.

FIG. 2 shows a diagrammatic view of an occlusion device 40 deployed within the LAA 42. As illustrated in FIG. 2, the LAA is a small cavity that is thumb-like in shape and is located off the left atrium. Shown is the occlusion device 40 comprising a plurality of ribs 44, a center post 46, a sheet 48, and a grasping knob 50. To secure the occlusion device 40 in the LAA 42, the ribs 44 exert a radial force which presses outwards against the walls of the LAA 42.

Though the shape of the device may vary somewhat, the device 40 is preferably shaped to fit in the LAA 42 so that it remains securely deployed and prevents blood from entering or exiting the LAA 42. As such, suitable shapes for the device generally resembles a pear. Once the device 40 is deployed, the cavity of the LAA 42 is occluded and thus, new thrombi cannot form in the LAA 42. Further, because the LAA 42 is occluded, existing thrombi cannot exit the LAA 42. Because thrombi cannot form in the LAA 42 and existing thrombi cannot exit the LAA 42, the occlusion device 40 helps to minimize the incidence of stroke.

Figure 3:
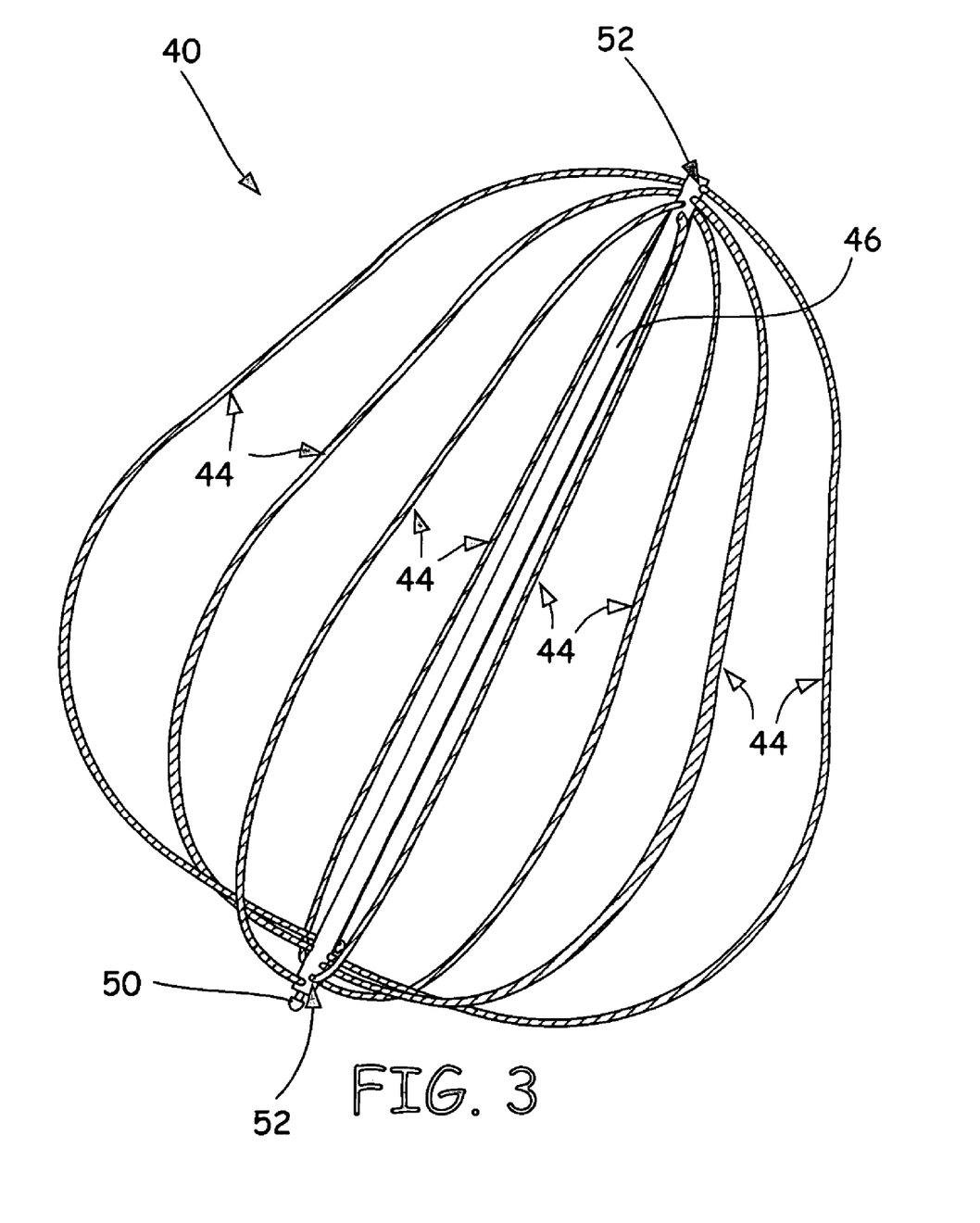
FIG. 3 is a perspective view of the frame of an occlusion device for the left atrial appendage shown without a sheet attached.

FIG. 3 is a side perspective view of an occlusion device 40 shown without a sheet to allow the frame of the device 40 to be more easily viewed. Shown is the occlusion device 40, the ribs 44, the center post 46, and the grasping knob 50. The center post 46 comprises a plurality of holes 52 located on each end of the center post 46.

As mentioned, the device 40 is configured to be deployed through a catheter. The knob 50 on the center post 46 is configured to allow the device 40 to be grasped by forceps as it is guided through the catheter. Only one side of the center post 46 requires a knob 50 because the device 40 needs only one attachment side for delivery and deployment or retrieval. Additionally, the device 40 is constructed so that the ribs 44 are easily collapsible about the center post 46 to allow the device to fit within a small diameter catheter. The ribs 44 are flexible and are capable of collapsing toward the center post 46. However, because the length of the ribs 44 is longer than the length of the center post 46, there is excess length in the ribs 44 as the ribs 44 collapse towards the center of the center post 46. Thus the ribs 44 also collapse slightly clockwise around the center post 46 to allow the device 40 to fit inside a small diameter catheter necessary for delivery. The mass of the device 40 should be kept to a minimum to allow the device 40 to be passed through a small diameter catheter and thus, unnecessary ribs should not be added.

The ribs 44 are constructed of a wire 48 which is threaded though the holes 52 in the center post 46. There are holes 52 located on the top and bottom of the center post 46. To create the ribs 44, the wire 48 is threaded through the holes 52 on the top of the center post 46 to the holes 52 on the bottom of the center post 46. More specifically, the wire 48 originates from the top end of the center post 46 and then extends to the bottom end of the center post 46 where it is threaded through a hole 52 in the center post 46. The wire 48 may then extend back to the end where it originated and be threaded through a hole 52 in that end of the center post. Thus, the wire 48 emanates from one end of the center post 46 and may be threaded through the center post 46 as many times as necessary to create the desired number of ribs 44. The end of the wire 48 may be welded to the center post 46 or tucked into a hole 52 in the center post 46 to secure it. In the present embodiment, eight ribs 44 are shown but the invention is not so limited. The device may comprise any number of ribs 44 so long as the ribs 44 are able to provide enough radial pressure to secure the device in the LAA. Additionally, the center post 46 must contain the appropriate number of holes 52 to create the desired number of ribs 44. For instance, to create eight ribs 44, each end of the center post 46 must have four holes 52.

The ribs 44 may also be created from multiple wires. Each wire end, however would need to be secured at the center post 46 individually. The ends may be secured by welding or other suitable methods which may require additional mass to secure the ends. Forming the ribs 44 out of multiple wires may also require additional holes 52 in the center post 46, which may weaken the center post 46.

The wire used to form the ribs 44 is preferably subjected to a precise pre-shaping to give the ribs 44 a "shape memory." The pre-shaping can be accomplished using any suitable method, such as machining, heat treating, or both. To further ensure that the ribs 44 do not suffer from fatigue failures, one embodiment of the present invention relies on making the ribs 44 of stranded wire or cables. The stranded wire used in this embodiment comprises a single inner wire wrapped by 7 additional wires, which are wrapped by 19 additional wires. The shape memory may further help to hold the strands together when the ribs 44 are formed of stranded wire or cable, and can be used to add pretension to the ribs 44 so that they "remember" their shape even after undergoing a strong deformation when the device 40 is passed through a catheter. The wire 48 may be made of a suitable material capable of shape memory, such as nickel-titanium alloy, commonly called Nitinol. Nitinol is preferably used because it is commercially available, very elastic, non-corrosive and has a fatigue life greater than that of stainless steel. However, the invention is not limited to these materials and any suitably biocompatible materials may suffice.

Figure 4:
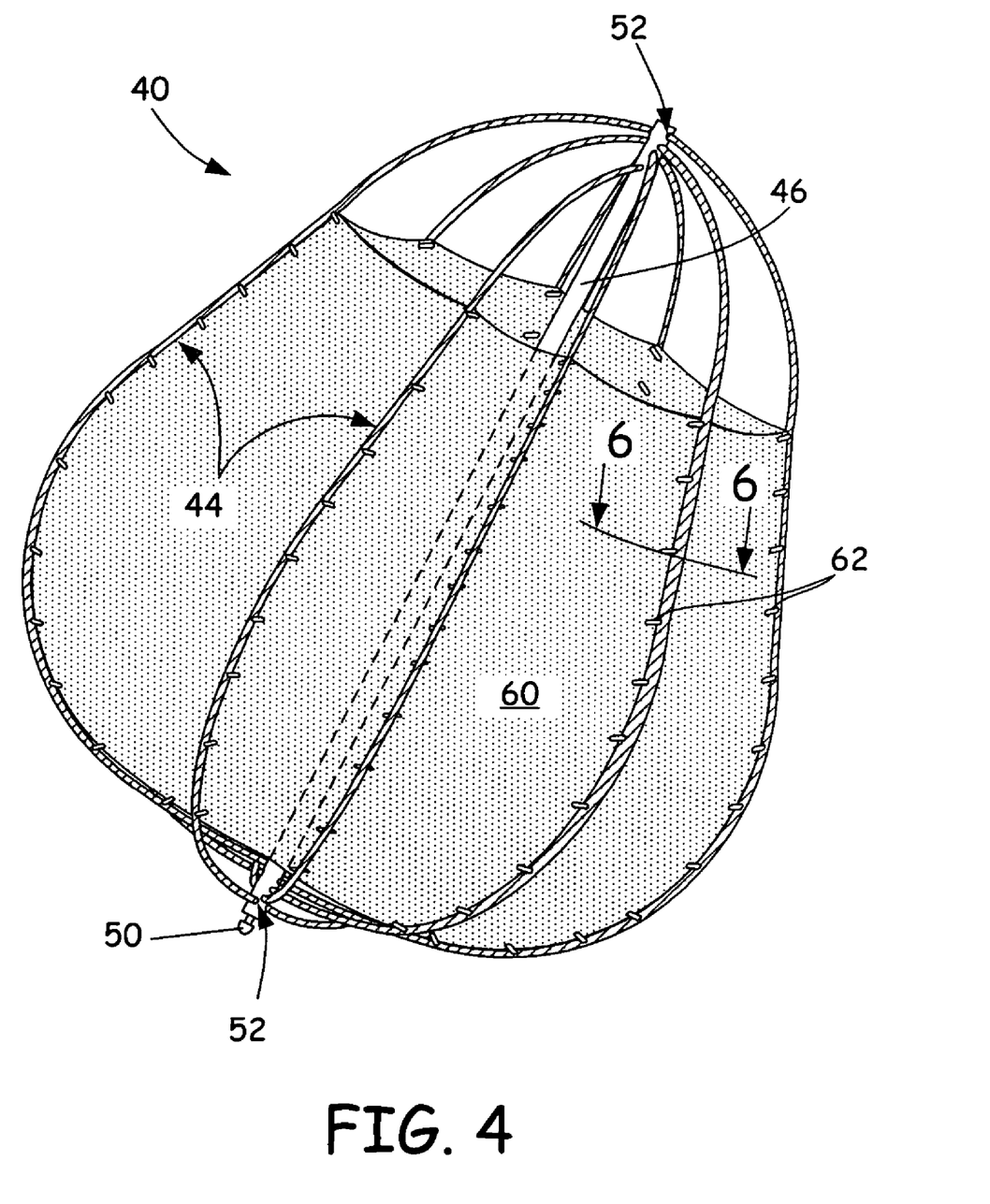
FIG. 4 is a perspective view of an occlusion device for the left atrial appendage.

FIG. 4 is a perspective side view of an occlusion device for the LAA. Shown is the occlusion device 40 comprising a plurality of ribs 44, the center post 46, a sheet 60, and the grasping knob 50. The sheet 60 is attached to the interior side of the device 40 using sutures 62 and covers approximately three quarters of the device frame in this embodiment. Alternately, the sheet 60 could be attached to the outside of the device 40, if desired. The sutures 62 secure the sheet 48 to the ribs 44 and prevent the sheet 60 from sliding up or down on the occlusion device 40. Alternately, the sheet 60 may also be attached to the ribs 44 using any suitable method, such as lamination.

The sheet 60 provides the device 40 with a barrier that prevents blood from entering or exiting the LAA. The sheet 60 is preferably formed of a medical grade polymer. Suitable materials include DACRON®, GORTEX®, or high density polyvinyl alcohol (PVA) foam. Preferably, the sheet 60 is formed of a high density PVA foam, such as that offered under the trademark IVALON®, which provides a matrix into which newly formed tissue may grow. To minimize the chance of the device 40 causing a blood clot, the sheet 60 may be treated with a thrombosis-inhibiting material. One such suitable material is heparin. The sheet 60 may extend from the end of the center post 52 having the grasping knob 50 to the other end of the device 40. Alternatively, the sheet 60 may extend only part way up the device 40 frame.

Figures 5A, 5B:
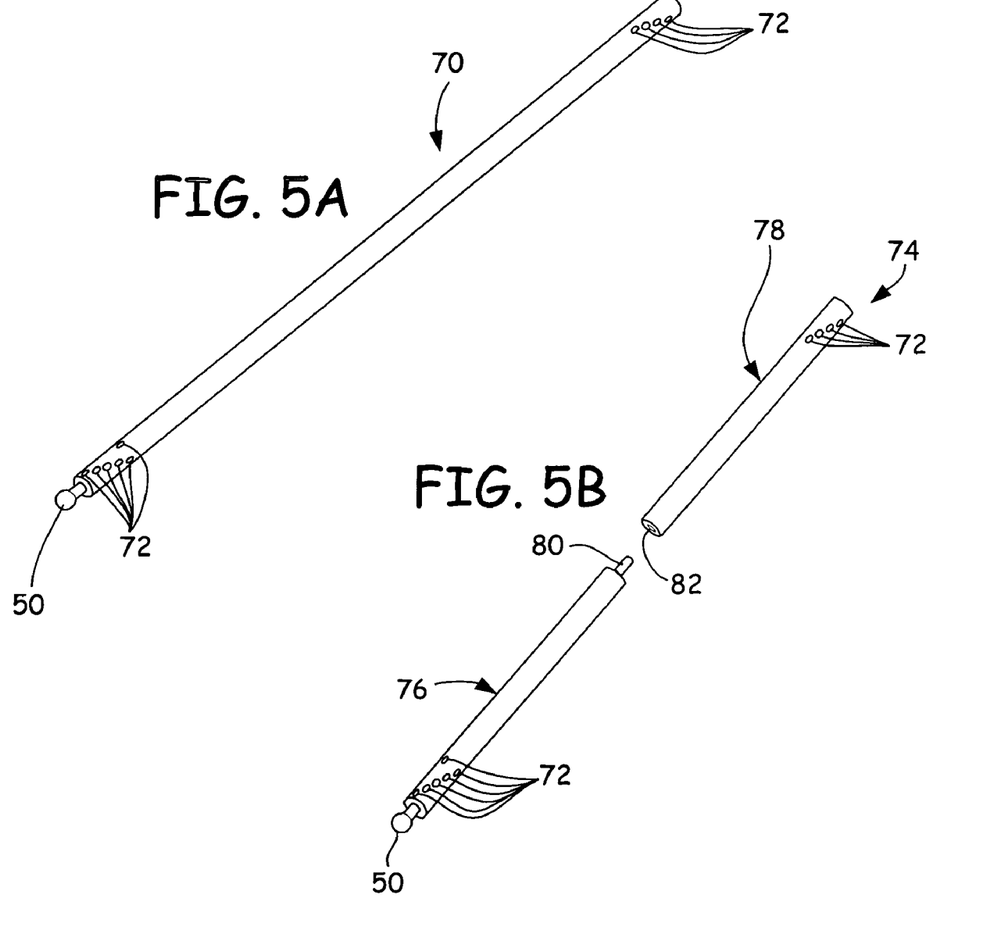
FIG. 5A is perspective side view of a center post.
FIG. 5B is a perspective side view of a center post having two segments.

FIGS. 5A and 5B are perspective side views of center posts for use with the present invention. FIG. 5A shows a center post 70 having a plurality of drill holes 72 in each end and a grasping knob 50 located on one end. FIG. 5B shows a split center post 74 having a first segment 76 and a second segment 78. Each segment has a plurality of drill holes 72 at one end. The drill holes 72 may be oriented anywhere from 10° to 80° from the adjacent drill holes 72. Additionally, the drill holes 72 should be somewhat staggered along the length of the center post 70, 72 so that the strength of the ends of the center post 70, 72 is not compromised. The center post 70, 74 may be anywhere from about 5 mm to about 40 mm long. The size of the center post 70, 74 may vary depending on the size of the patient's LAA. The center post 70, 74 may be constructed of titanium or any other suitable biocompatible material.

The knob 50 on the center post 70, 74 is configured to allow the device 40 to be grasped by a forceps as it is guided through the catheter. However, the method of attachment to a delivery device is not so limited. The knob 50 may be modified as needed to attach to any delivery device. For instance, the knob 50 may be fitted with threads so that it may be screwed onto a delivery device that is outfitted with threads. As mentioned, only one side of the device 40 requires a knob 50 or other mechanism to attach to a delivery device.

The split center post 74 shown in FIG. 5B is advantageous because the mass of the device 40 is reduced by eliminating a portion of the metal comprising a center post. Additionally, the split center post 74 may provide improved loading, deployment, and navigational capabilities. In the split center post 74, the first segment 76 has a grasping knob 50 located on one end. In addition, the first segment 76 has a pin 80 which reversibly connects with a lumen 82 on the second segment 78. To advance the device 40 through a catheter, a delivery forceps or other delivery device attaches to the grasping knob 50 on the center post 74. To move the device 40 through the catheter, the delivery device, such as a forceps, pushes the device 40 using the both the first and second segments 76, 78. For this reason, the first segment 76 is equipped with a pin 80 that fits into a lumen 82 extending into the second segment 78. When pushing the device 40 through the catheter, the pin 80 connects with the lumen 82 of the second segment 78.

The connection between the first and second segments 76, 78 improves the navigability of the device 40 and reduces the chances of accidental perforation of tissue. In particular, the connection of the lumen 82 to the pin 80 improves navigability by making it easier to "steer" the device 40 when the physician advances and maneuvers the device 40 through the body to the treatment site. When the pushing ceases or when the device 40 is pulled, the first and second segments 76, 78 separate. Thus, when the first segment 76 is pulled, the two segments 76, 78 are no longer in direct contact. The segments 76, 78, however, remain connected by the ribs, which are threaded through holes 72 in the segments 76, 78. Therefore, the device 40 moves as a whole even though the two segments 76, 78 are not permanently connected. In addition, even though the split center post 74 is capable of moving as a whole, the split center post 74 has more flexibility than the solid center post 70 because the segments 76, 78 are capable of separating from one another and thus, providing a joint. The flexibility of the split center post 74 makes it easier to maneuver through a catheter and reduces the chance of accidental perforation of tissue once the device 40 is deployed.

Figure 6:
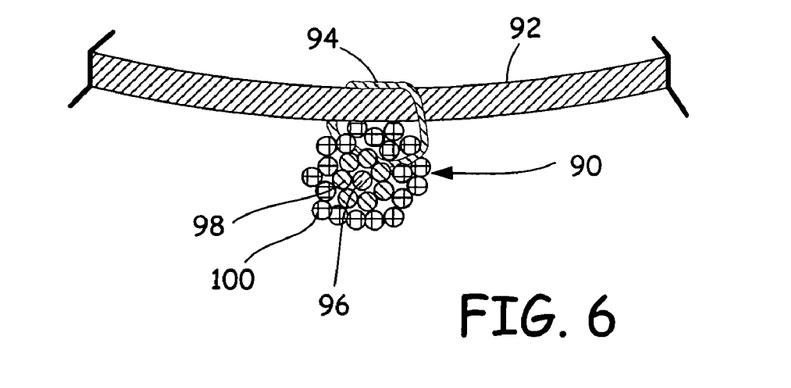
FIG. 6 is an enlarged view of a stranded wire arm with a sheet sutured to the stranded wire arm.

FIG. 6 is a cross sectional view, as taken from FIG. 4, of a stranded wire rib 90, a portion of a sheet 92, and a suture 94. As mentioned previously, the ribs 90 are constructed of stranded wire so the ribs 90 are less likely to suffer breakage from fatigue. Thus, the stranded wire which is used to construct the ribs 90 comprises a center strand 96 wrapped by 7 additional strands 98, which are in turn wrapped by 17 additional strands 100. When the sheet 92 is sutured to the rib 90, the suture 94 goes through the sheet 92 and may be threaded through the stranded wire rib 90. Because the suture 94 goes through the stranded wire rib 90, the suture 94 does not slide up or down on the stranded wire rib 90. If the suture 94 was able to slide up or down the stranded wire rib 90, the sheet 92 may bunch up as the occlusion device is advanced through a catheter. If the sheet 92 bunches as the occlusion device is advanced through a catheter, the ease of deployment and the device's occluding ability may be compromised.

Figure 7:
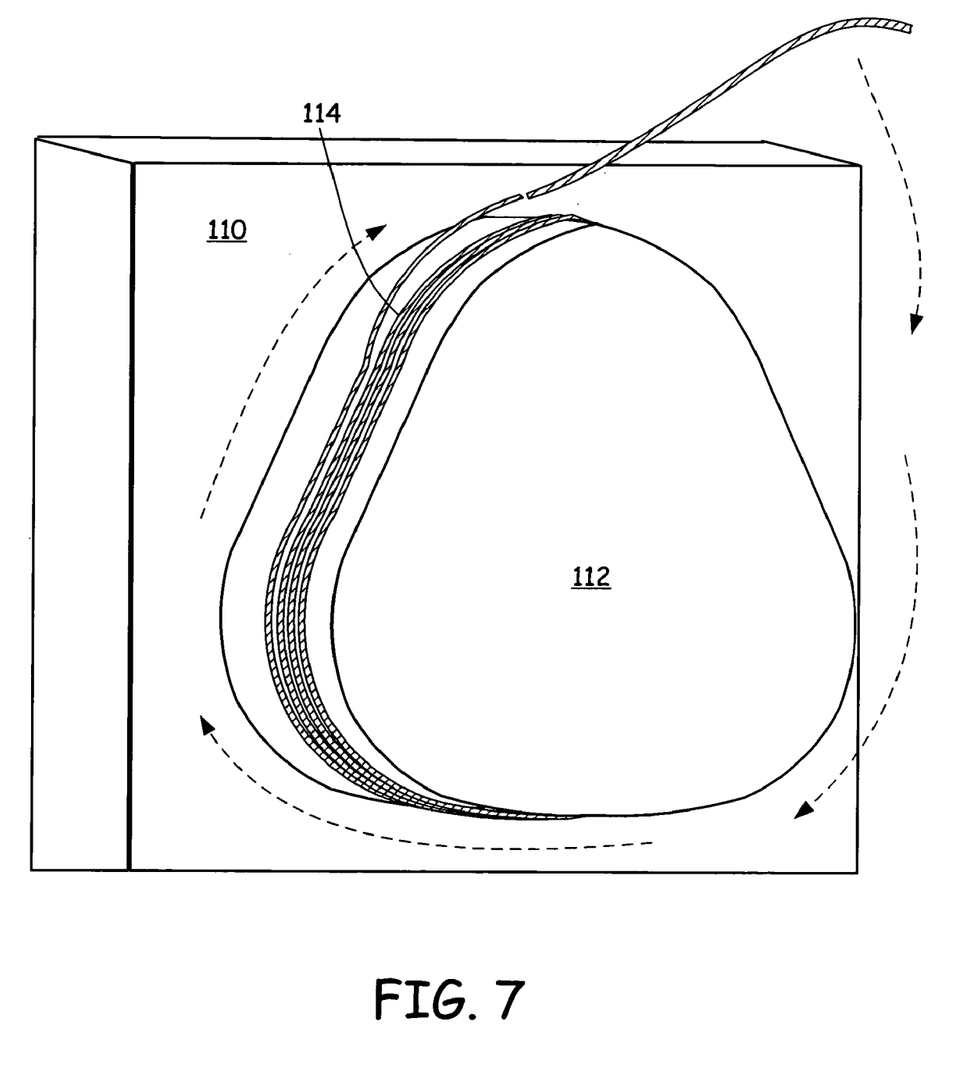
FIG. 7 is a diagram of one method for heat shaping stranded wire for use in the occlusion device.

As mentioned previously, the stranded wire that forms the ribs may be heat shaped. FIG. 7 demonstrates one method of heat shaping a stranded wire. Shown is a block 110 having a shaping form 1.12, which is mounted to the block 110 and a stranded wire 114 which is wrapped around the shaping form 112. The stranded wire 114 is wrapped around the shaping form 112 and then heated. After the stranded wire 114 cools, the stranded wire 114 is removed from the block 110 and can then be attached to the device. Each time the stranded wire 114 is wrapped around the shaping form 112 a set of two ribs is formed. Thus, to form eight ribs, the stranded wire 114 should be wrapped around the shaping form 112 four times.

The shape of the shaping form 112 shown in FIG. 7 may be altered to vary the shape of the device. A circular shaping form may be used to create a more circular device frame. In the embodiment shown in the previous figures, a pear shaped device frame is shown, and thus, the shaping form 112 is constructed to shape the wire arm 114 to form a pear-like shape.

Although the present invention has been described with reference to preferred embodiments, workers skilled in the art will recognize that changes may be made in form and detail without departing from the spirit and scope of the invention.

The invention claimed is:

1. An occlusion device for occluding a left atrial appendage, the occlusion device comprising:
    a center post having a proximal end and a distal end;
    a plurality of ribs extending radially outward from the proximal end of the center post to the distal end of the center post to form a frame, wherein a diameter of the frame near the proximal end of the center post is greater than a diameter of the frame near the distal end of the center post and is shaped to securely fit within a left atrial appendage; and
    a PVA foam sheet attached to the ribs, the sheet extending between the ribs and forming a sack shaped barrier supported by the ribs that is closed at the proximal end and extends toward the distal end a distance sufficient to close an entrance to the left atrial appendage and to prevent blood from entering or exiting the left atrial appendage.

2. The occlusion device of claim 1 wherein the center post is formed of titanium.

3. The occlusion device of claim 1 wherein the center post comprises two segments.

4. The center post of claim 3 wherein a first segment of the center post comprises a pin and a second segment of the center post comprises a lumen and wherein the pin of the first segment connects with the lumen of the second segment.

5. The occlusion device of claim 1 wherein the center post further comprises holes through which the ribs attach.

6. The occlusion device of claim 1 wherein the center post is about 5 to about 40 mm long.

7. The occlusion device of claim 1 wherein the ribs are constructed of stranded wire.

8. The occlusion device of claim 7 wherein the stranded wire is heat shaped.

9. The occlusion device of claim 1 wherein the ribs are constructed of a single stranded wire.

10. The occlusion device of claim 9 wherein the stranded wire is heat shaped.

11. The occlusion device of claim 1 wherein the sheet is attached to the ribs with sutures.

12. The occlusion device of claim 1 wherein the sheet is laminated to the ribs.

13. The occlusion device of claim 1 wherein the sheet is treated to be non-thrombogenic.

14. A collapsible occlusion device for insertion into a left atrial appendage of a human heart, the device comprising:
- a center post having a proximal end and a distal end, wherein both the proximal end and the distal end comprise a plurality of holes;
- a single stranded wire threaded through holes in the distal and proximal ends of the center post to form a plurality of ribs, wherein the plurality of ribs define a frame having a diameter near the proximal end of the center post that is larger than a diameter near the distal end of the center post and is shaped to securely fit within a left atrial appendage; and
- a foam sheet attached to the plurality of ribs, the sheet extending between the ribs and forming a sack shaped barrier supported by the ribs that is closed at the proximal end and extends toward the distal end a distance sufficient to close an entrance to the left atrial appendage and to prevent blood from entering or exiting the left atrial appendage.

15. The occlusion device of claim 14 wherein the center post comprises a grasping knob.

16. The occlusion device of claim 14 wherein the center post is formed of titanium.

17. The occlusion device of claim 14 wherein the center post comprises two segments.

18. The center post of claim 17 wherein a first segment of the centerpost comprises a pin and a second segment of the center post comprises a lumen and wherein the pin of the first segment connects with the lumen of the second segment.

19. The occlusion device of claim 14 wherein the center post is about 5 to about 40 mm long.

20. The occlusion device of claim 14 wherein the ribs are heat shaped.

21. The occlusion device of claim 14 wherein the sheet is constructed of PVA foam.

22. The occlusion device of claim 14 wherein the sheet is attached to the ribs with sutures.

23. The occlusion device of claim 14 wherein the sheet is laminated to the ribs.

24. The occlusion device of claim 14 wherein the sheet is treated to be non-thrombogenic.

25. A left atrial appendage occlusion device comprising:
- a center post comprising a proximal end, a distal end, and a graspable component;
- a plurality of holes located in the proximal end of the center post;
- a plurality of holes located in the distal end of the center post;
- a single wire extending from the proximal end of the center post to the distal end of the center post and passing through holes in the distal end of the center post and proximal end of the center post to form a plurality of ribs, wherein the plurality of ribs define a frame having a diameter near the proximal end of the center post that is larger than a diameter near the distal end of the center post and is shaped to securely fit within a left atrial appendage; and
- a foam sheet attached to the plurality of ribs, the sheet extending between the ribs and forming a sack shaped barrier supported by the ribs that is closed at the proximal end and extends toward the distal end a distance sufficient to close an entrance to the left atrial appendage and to prevent blood from entering or exiting the left atrial appendage.

26. The occlusion device of claim 25 wherein the center post is formed of titanium.

27. The occlusion device of claim 25 wherein the center post comprises two segments.

28. The center post of claim 27 wherein a first segment of the center post comprises a pin and a second segment of the center post comprises a lumen and wherein the pin of the first segment connects with the lumen of the second segment.

29. The occlusion device of claim 25 wherein the length of the center post is about 5 to about 40 mm long.

30. The occlusion device of claim 25 wherein the ribs are constructed of stranded wire.

31. The occlusion device of claim 25 wherein the ribs are heat shaped.

32. The occlusion device of claim 25 wherein the foam sheet is constructed of PVA foam.

33. The occlusion device of claim 25 wherein the foam sheet is attached to the ribs by sutures.

34. The occlusion device of claim 25 wherein the foam sheet is attached to the ribs by heat laminating.

35. The occlusion device of claim 25 wherein the foam sheet is treated to be non-thrombogenic.

36. An occlusion device for occluding a left atrial appendage, the occlusion device comprising:
- a center post having a proximal end and a distal end;
- a plurality of ribs extending radially outward from the proximal end of the center post to the distal end of the center post to create a generally pear shaped frame, wherein a diameter of the frame near the proximal end of the center post is greater than a diameter of the frame near the distal end of the center post and is shaped to securely fit within a left atrial appendage; and
- a sheet formed of a medical grade polymer attached to the ribs, the sheet extending between the ribs and forming a sack shaped barrier supported by the ribs that is closed at the proximal end and extends toward the distal end a distance sufficient to close an entrance to the left atrial appendage and to prevent blood from entering or exiting the left atrial appendage.

37. The occlusion device of claim 36 wherein the center post is formed of titanium.

38. The occlusion device of claim 36 wherein the center post comprises two segments.

39. The center post of claim 36 wherein a first segment of the center post comprises a pin and a second segment of the center post comprises a lumen and wherein the pin of the first segment connects with the lumen of the second segment.

40. The occlusion device of claim 36 wherein the center post further comprises holes through which the ribs attach.

41. The occlusion device of claim 36 wherein the center post is about 5 to about 40 mm long.

42. The occlusion device of claim 36 wherein the ribs are constructed of a single stranded wire.

43. The occlusion device of claim 36 wherein the ribs are heat shaped.

44. The occlusion device of claim 36 wherein the sheet is constructed of PVA foam.

45. The occlusion device of claim 36 wherein the sheet is attached to the ribs with sutures.

46. The occlusion device of claim 36 wherein the sheet is laminated to the ribs.

47. The occlusion device of claim 36 wherein the sheet is treated to be non-thrombogenic.

* * * * *